United States Patent [19]
Klibanov et al.

[11] Patent Number: 4,826,762
[45] Date of Patent: May 2, 1989

[54] ENZYMATIC TEMPERATURE CHANGE INDICATOR

[75] Inventors: Alexander M. Klibanov, Newton, Mass.; Jonathan S. Dordick, Iowa City, Iowa

[73] Assignee: Massachusetts Industry of Technology, Cambridge, Mass.

[21] Appl. No.: 112,893

[22] Filed: Oct. 23, 1987

[51] Int. Cl.$^4$ .................. C12Q 1/28; G01K 11/06
[52] U.S. Cl. .................... 435/28; 435/3,25; 435/810; 426/88; 374/106; 374/160; 116/207; 116/217
[58] Field of Search .................. 116/207, 206; 435/25, 435/189, 28, 810; 426/88

[56] References Cited

U.S. PATENT DOCUMENTS

| | | | |
|---|---|---|---|
| 2,553,369 | 5/1951 | Hoffman | 374/106 X |
| 2,671,028 | 3/1954 | Clark | 374/106 X |
| 3,956,153 | 5/1976 | Chadha | 116/207 X |
| 4,291,122 | 9/1981 | Orelski | 435/31 |
| 4,579,823 | 4/1986 | Ryder | 435/810 X |
| 4,716,101 | 12/1987 | Thompson et al. | 435/4 |
| 4,740,465 | 4/1988 | Suzuki | 435/25 X |

FOREIGN PATENT DOCUMENTS 1366797 9/1974 United Kingdom .

OTHER PUBLICATIONS

Boeriu et al., *BioTechn.*, "Enzymatic Reactions in Liquid and Solid Paraffins: Application for Enzyme-Based Temperature Abuse Sensors", 4 (11/86), 2 pages.

*Primary Examiner*—Daniel M. Yasich

[57] ABSTRACT

A temperature change indicator is described which is composed of an enzyme and a substrate for that enzyme suspended in a solid organic solvent or mixture of solvents as a support medium. The organic solvent or solvents are chosen so as to melt at a specific temperature or in a specific temperature range. When the temperature of the indicator is elevated above the chosen, or critical temperature, the solid organic solvent support will melt, and the enzymatic reaction will occur, producing a visually detectable product which is stable to further temperature variation.

8 Claims, 1 Drawing Sheet

ENZYMATIC TEMPERATURE CHANGE INDICATOR

BACKGROUND OF THE INVENTION

The Government has rights in this invention pursuant to Contract Number 957381 awarded by the Department of Energy.

This invention relates to indicators of temperature change over time which are used to monitor the shipping and handling conditions of perishable items.

When perishable items are shipped long distances for distribution, it is usual to monitor the shipping and handling conditions to be able to have information about the quality of the delivered product. Numerous devices have been patented in order to meet this need. One class of devices measures the diffusion of dyes or oils, e.g., up a wick, or the amount of mechanical deformation of an object, e.g., a thin metal strip, as the ambient temperature rises. Another class contains capsules that rupture upon freezing to activate the device. The compounds in the device react to cause a color change, very slowly while the components are still frozen but much more quickly if the temperature should become elevated.

There are several patented devices that use the action of an enzyme on a substrate to produce a color change as the temperature increases. Hoffman, U.S. Pat. No. 2,553,369 teaches the use of a starch digesting enzyme to hydrolyze a starch-indole complex so that its characteristic color disappears. These components are dissolved in a water solution. In the device of Clark, U.S. Pat. No. 2,671,028, the action of the enzyme on the substrate with increasing temperature causes a change in pH, thereby triggering a color change in an indicator. These components are again in a water solution. In GB Pat. No. 1,366,797 the device which is activated upon freezing contains, in a water solution, appropriate enzyme and substrate to produce ammonia gas which diffuses through a semipermeable diaphragm whose permeability increases with an increase in temperature. The ammonia reacts with a pH indicator on the other side of the diaphragm.

SUMMARY OF THE INVENTION

One aspect of the invention generally features a temperature change indicator which is composed of an enzyme and a substrate for that enzyme suspended in a solid organic solvent or mixture of solvents as a support medium. The organic solvent or solvents are chosen so as to melt at a specific temperature or in a specific temperature range. When the temperature of the indicator is elevated above the chosen, or critical temperature, the solid organic solvent support will melt, and the enzymatic reaction will occur, producing a visually detectable product which is stable to further temperature variation.

In preferred embodiments of the invention the indicator includes a buffering system, the organic solvent is a paraffin or a mixture or paraffins, the enzyme is peroxidase, and the substrates are peroxide and p-anisidine.

The indicator is packaged and attached to perishable items, e.g., pharmaceuticals, biologicals, or foodstuffs, and the melting temperature of the solid organic solvent or mixture of solvents is chosen to be the point above which it is undesirable to elevate the temperature of the perishable items (two preferred temperatures are $-5°$ C. and $10°$ C.).

The invention gives the temperature indicator a very long useful lifetime as the enzymatic reaction rate in a solid organic solvent support medium is many orders of magnitude slower than it would be in a liquid organic solvent at that same temperature. A mixture of organic solvents can be prepared to obtain a support medium with almost any desired melting point including temperatures well below or well above $0°$ C. where an aqueous indicator system would not be useful. No preconditioning of the indicator is necessary before use.

Other features and advantages of the invention will be apparent from the following description of the preferred embodiments thereof and from the claims.

DESCRIPTION OF THE PREFERRED EMBODIMENTS

Figure 1:
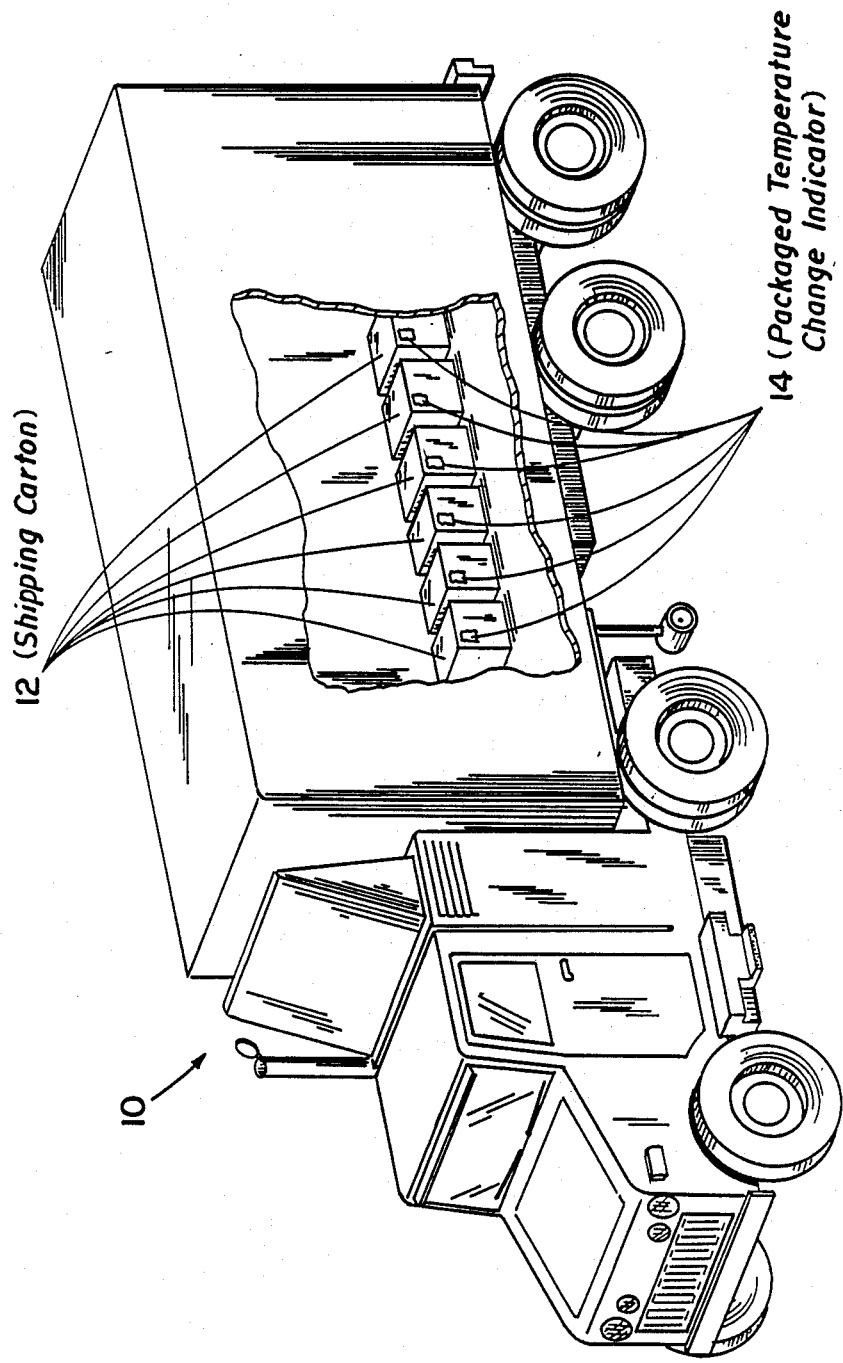

We first briefly describe FIG. 1.

FIG. 1 illustrates in schematic fashion a transport vehicle partially cut away, containing cartons of perishable items which each has attached a packaged indicator of the invention.

One temperature change indicator according to the invention can be prepared in the following manner.

In the description below the term paraffin is used for any one or a mixture of long-chain alkanes.

Horseradish peroxidase (Sigma) (0.2 mg) was deposited onto 45 mg of glass beads (non-porous, 75-150 microns) according to the method of Kazandjian et al. (1986) Biotechnol. Bioeng. 28: 417-421. The enzyme coated beads were added to 9 ml of molten hexadecane containing 10 mM p-anisidine. The suspension was poured into a culture dish ($60 \times 15$ mm) and placed in a refrigerator. Following solidification, 1 ml of hexadecane containing 10 mM p-anisidine and 50 ul of 200 mM $H_2O_2$ in 10 mM aqueous phosphate buffer (pH 7.0) was poured on top of the first hexadecane layer and allowed to solidify in a refrigerator. The added water was adsorbed by the surface of the glass beads or the walls of the vessel so that the solvent in which the beads were suspended was always monophasic. The dish was sealed with Parafilm and stored at $4°$ C. Virtually no color developed under these conditions even after 21 days. However, when that dish was placed at room temperature for just one hour (during which time the paraffin melted), the reaction mixture acquired a distinctive reddish-brown color which it retained even when the mixture had been returned to $4°$ C. and resolidified.

The increase in reaction rate of the enzyme as the support medium is changed from a solid to a liquid is orders of magnitude greater than would occur if the enzyme and substrate underwent the same temperature change in an organic solvent which was liquid at both temperatures. For the reaction described above, the peroxidase-catalyzed oxidation of p-anisidine, no appreciable reaction was observed in solid hexadecane at $4°$ C.; after several days the mixture remained white. However, at $25°$ C. the liquid reaction mixture turned its distinctive color in a few minutes. The reaction at $25°$ C. was calculated to be $4.5 \times 10^6$ times faster than at $4°$ C. This same phenomenon was also observed when the above reaction was carried out in pentadecane and in a 1:1 mixture of hexadecane and pentadecane.

However, when the same enzymatic reaction was carried out in hexane, which is liquid at both $4°$ C. and $25°$ C., the difference in the enzymatic reaction rates at the two temperatures was less than 2.5 fold. Further experiments designed to elucidate the cause of the difference in reaction rates established that the drastically lower reaction rate in the solid organic solvent compared to liquid was due to an alteration of the catalytic power of the enzyme (as reflected by $k_{cat}$) rather than of enzyme-substrate binding (as reflected by $K_m$).

The same system as above was also used with another enzyme, mushroom polyphenol oxidase. This enzyme oxidized p-anisidine with $O_2$ in hexadecane at 25° C. $2.4 \times 10^4$ times faster than at 4° C. (in hexane the difference was only 2.5 fold).

Many other organic solvents or mixtures of solvents can be used as support media for the indicator of the invention. For example, alkanes of the general formula $C_nH_{2n+2}$ have a wide variety of melting points, some of which are listed below:

| compound | | m.p. °C. |
|---|---|---|
| hexane, | C=6 | −95 |
| octane, | C=8 | −56.8 |
| decane, | C=10 | −29.7 |
| dodecane, | C=12 | −9.6 |
| tridecane, | C=13 | −5.5 |
| tetradecane, | C=14 | 5.9 |
| pentadecane, | C=15 | 10 |
| hexadecane, | C=16 | 18.2 |
| octadecane, | C=18 | 28.2 |
| eicosane, | C=20 | 36.8 |
| triacontane, | C=30 | 65.8 |

(from the *Handbook of Chemistry and Physics*, 63rd edition, 1983)

Mixtures of solvents of any appropriate melting point can be prepared by a suitable combination of the individual compounds. One particularly useful melting point is −5° C. for an indicator that will show if frozen food intended to be stored in deep cold storage, −20° C., has exceeded its safe limit. Another useful melting point is 10° C. as an indicator of whether items that must be chilled (but not frozen), such as aqueous solutions of antibiotics and vaccines, have been handled properly.

Use

The temperature change indicators of the invention can be used as monitors of shipping and handling conditions of a wide range of perishable items. FIG. 1 shows a truck 10 carrying cartons 12 of perishable items, each of which has attached a temperature change indicator 14 packaged in a convenient form. The devices will indicate when a previously determined critical time-temperature relationship has been exceeded. For example, cultures of microorganisms, growth hormones and other protein drugs such as insulin and tissue plasminogen activator must be shipped and stored under controlled conditions. Some antibiotics and vaccines require constant refrigeration during shipment. Others can tolerate some warmth but not excessive heat. Most non-processed food items have a critical elevated temperature and time relationship that should not be exceeded for preservation of maximum quality. It may be useful to attach several indicators, whose critical temperatures vary, to one package. In that way, for example, the receiver of a particular product, e.g., frozen hamburger, would known that while the product may not have the best taste, it would still be safe to eat.

Other Embodiments

In other embodiments of the invention visual identification of a product could be afforded by a response to a pH change that was caused by enzymatically produced acid or alkali. Other enzyme-substrate combinations where the color change was caused by any oxidation, or reduction, or other effect of the enzyme on the substrate could also be used.

Other features and embodiments are within the following claims.

We claim:

1. A temperature change indicator comprising
   an enzyme and a substrate of said enzyme, wherein the reaction of said substrate catalyzed by said enzyme produces a visually detectable product, said enzyme and said substrate being suspended in a solid organic solvent or mixture of solvents as a support medium, said solvent or mixture of solvents being chosen so as to melt at a specific temperature or in a specific temperature range,
   whereby when the temperature of said indicator is elevated above said specific temperature or to within said specific temperature range, said solvent or solvents melts, allowing said reaction to occur wherein said visually detectable product is produced, said product being stable to further temperature variation.

2. The indicator of claim 1, further comprising a buffering system.

3. The indicator of claim 1 wherein said organic solvent is a paraffin or a mixture of paraffins.

4. The indicator of claim 1 wherein said enzyme is peroxidase, said substrate is peroxide, and said indicator further comprises p-anisidine.

5. The indicator of claim 1 wherein said indicator is packaged and attached to perishable items, e.g., pharmaceuticals, biologicals, or food stuffs.

6. The indicator of claim 5 wherein said melting temperature of said solid organic solvent or mixture of solvents is chosen to be the point above which it is undesirable to elevate the temperature of said perishable items.

7. The indicator of claim 1 wherein said melting temperature of said solid organic solvent or mixture of solvents is about −5° C.

8. The indicator of claim 1 wherein said melting temperature of said solid organic solvent or mixture of solvents is about 10° C.

* * * * *

UNITED STATES PATENT AND TRADEMARK OFFICE
CERTIFICATE OF CORRECTION

PATENT NO. : 4,826,762
DATED : May 2, 1989
INVENTOR(S) : Alexander M. Klibanov et al.

It is certified that error appears in the above-identified patent and that said Letters Patent is hereby corrected as shown below:

Column 1, line 60, change "or" (second occurrence) to --of--.

Column 4, line 5, change "known" to --know--.

Signed and Sealed this

Ninth Day of January, 1990

Attest:

JEFFREY M. SAMUELS

*Attesting Officer*  *Acting Commissioner of Patents and Trademarks*